United States Patent
Tucker, Jr.

(10) Patent No.: US 11,439,924 B2
(45) Date of Patent: Sep. 13, 2022

(54) METHOD FOR IMPROVING WATER BALANCE AND/OR EFFICIENCY IN ETHANOL PRODUCTION

(71) Applicant: Kinergetics LLC, Madison, WI (US)

(72) Inventor: Charles Thomas Tucker, Jr., Madison, WI (US)

(73) Assignee: Kinergetics LLC, Madison, WI (US)

(*) Notice: Subject to any disclaimer, the term of this patent is extended or adjusted under 35 U.S.C. 154(b) by 0 days.

(21) Appl. No.: 17/230,609

(22) Filed: Apr. 14, 2021

(65) Prior Publication Data
US 2021/0316227 A1 Oct. 14, 2021

Related U.S. Application Data

(60) Provisional application No. 63/009,798, filed on Apr. 14, 2020.

(51) Int. Cl.
| | | |
|---|---|---|
| *B01D 1/14* | (2006.01) | |
| *C12F 3/10* | (2006.01) | |
| *C07C 29/78* | (2006.01) | |
| *B01D 1/16* | (2006.01) | |
| *B01D 1/06* | (2006.01) | |

(52) U.S. Cl.
CPC .............. *B01D 1/14* (2013.01); *B01D 1/065* (2013.01); *B01D 1/16* (2013.01); *C07C 29/78* (2013.01); *C12F 3/10* (2013.01)

(58) Field of Classification Search
CPC ...... C12F 3/00; C12F 3/06; C12F 3/08; C12F 3/10; C12H 6/02; B01D 1/065; B01D 1/14; B01D 1/16

USPC ......... 159/4.01, 4.02, 4.03, 4.04, 4.05, 4.06, 159/4.07, 4.08, 4.09, 4.1, 4.2, 4.3, 4.4
See application file for complete search history.

(56) References Cited

U.S. PATENT DOCUMENTS

| | | | | |
|---|---|---|---|---|
| 394,434 | A * | 12/1888 | Bassler | B01D 1/18 |
| | | | | 261/127 |
| 2,349,657 | A * | 5/1944 | Hermelin | B01D 1/065 |
| | | | | 159/13.3 |
| 2,434,672 | A * | 1/1948 | Pattee | C12F 3/10 |
| | | | | 159/47.1 |
| 5,439,701 | A * | 8/1995 | Zimlich, III | A23L 27/201 |
| | | | | 426/624 |
| 2008/0190416 | A1* | 8/2008 | Irisarri Navalpotro | F26B 3/12 |
| | | | | 127/30 |
| 2009/0263540 | A1* | 10/2009 | Allen | C12P 7/06 |
| | | | | 426/11 |
| 2013/0206342 | A1* | 8/2013 | Dahmes | C08J 11/04 |
| | | | | 159/4.01 |
| 2015/0045594 | A1* | 2/2015 | Overheul | C10G 3/42 |
| | | | | 585/240 |

* cited by examiner

*Primary Examiner* — Jonathan Luke Pilcher
(74) *Attorney, Agent, or Firm* — Boardman & Clark LLP (57) ABSTRACT

A method and system for balancing water content in a liquid mixture is described. The method includes using an direct column contact evaporator to reduce the water content in the liquid mixture. The liquid mixture is provided in the open column direct contact evaporator with relatively dry air. The dry air evaporates excess water from the liquid mixture to concentrate the liquid mixture while at the same time reducing the energy required for water evaporation elsewhere in the plant.

10 Claims, 5 Drawing Sheets

METHOD FOR IMPROVING WATER BALANCE AND/OR EFFICIENCY IN ETHANOL PRODUCTION

CROSS-REFERENCE TO RELATED APPLICATIONS

This application claims the benefit of U.S. Provisional Patent Application No. 63/009,798, filed on Apr. 14, 2020, entitled "METHOD FOR IMPROVING WATER BALANCE IN ETHANOL PRODUCTION," the entire content of which is hereby incorporated by reference herein in its entirety.

FIELD OF THE INVENTION

The present inventions relate to the field of ethanol production. The present inventions more specifically relate to the field of balancing water entering and leaving an ethanol plant, and/or improving plant thermal efficiency.

BACKGROUND

Nearly all ethanol plants struggle to maintain a proper balance of water entering and leaving their facilities while minimizing the energy required for evaporation and for drying when dryers are present. Some plants are able to discharge water to a city or other wastewater plant to help with the balance, and other plants allow the water to be eliminated either through what is called wet cake (wet distillers grains) or through dryers when the facility produces dry distillers grains (DDG). The wet distillers grains may have what is called "syrup" applied up stream of a dryer, in which case the dried grains are called dried distillers grains with solubles (DDGS). While the DDGS provide certain material benefits, water elimination from the syrup also occurs.

Thin stillage results when whole stillage from distillation is processed in decanters designed to separate suspended solids and water. Not all solids are removed, and the water that contains these solids, dissolved and suspended, is called thin stillage. The syrup applied to the wet grains results when some of the water in the thin stillage is evaporated. Ethanol plants typically use some form of falling film evaporation to remove this water. The more water that is removed from the thin stillage, the thicker and more viscous the syrup but less energy is required when dryers are used. Because the water being evaporated typically becomes process condensate, the plant water balance is also impacted.

Water removal and thus, syrup concentration is limited in the typical falling film evaporator due to increasing viscosity. While a high efficiency forced circulation evaporation system can allow a significantly greater syrup concentration to be obtained, these systems are expensive, can be costly to operate, and water balance is still impacted and must be addressed in one form or another.

Water balance can become even more of an issue when a facility expands its ethanol production. While existing evaporation systems may be modified to accommodate increased evaporation needs resulting from process expansion at a facility, the increased evaporation also leads to increased load on existing evaporation equipment and excess water that needs to be addressed to maintain an acceptable facility water balance. While traditional evaporation methods and equipment can be used to help address the water balance challenge, such an approach also requires a significant energy cost for system operation.

Accordingly, there is a need for an improved ethanol plant evaporation process that increase plant efficiency and/or reduces the Carbon Intensity (CI).

Accordingly, there is a need for an improved ethanol evaporation process that provides a more optimal water balance utilizing existing environmental controls. There is also a need for an improved ethanol process that allows for shorter delivery and construction times relative to typical evaporation equipment (i.e., falling film evaporators or other traditional evaporators that utilize heat exchangers with tubes, plates or other physical barrier between types of fluids). In particular, a preferred improved ethanol process requires less or minimal heat transfer surface, mass transfer packing, and/or heat transfer media, thereby reducing or minimizing component parts that are known to foul and plug, and may require less regular maintenance and cleaning, and thus, reduce the typical expense associated therewith.

There is also a need for an improved ethanol process that costs less to construct, install, operate and/or maintain relative to other known ethanol plants of similar capacity and/or process size. Additionally, there is a need for an improved ethanol process that, depending on the existing ethanol plant or process design, can be retrofit into the existing facility to reduce condensing load on existing evaporators, reduce the energy used to operate existing evaporators, and/or reduce bottlenecks in the existing evaporators to generally improve the overall plant energy balance and efficiency and/or Carbon Intensity. Thus, there is a need for an improved ethanol process and plant design that can improve water balance by utilizing what is typically considered excess or waste heat in a typical plant or process. There is also a need for an improved ethanol process and plant design that helps improve water balance while also improving the typical production process (e.g., by cooling and/or concentrating process fluids before or after a typical evaporation step or process is provided or applied, such as in a falling film evaporator).

SUMMARY

Improved ethanol plant designs, processes, and methods with improved evaporation and/or more optimal water balance are provided. In particular, the provided improved ethanol plant designs, processes and methods are relatively simple, cost effective and allow for shorter delivery and construction times relative to typical evaporation equipment (i.e., falling film evaporators or other evaporators which utilize heat exchangers with tubes, plates or other physical barrier between types of fluids).

Additionally, improved ethanol plant designs, processes and methods are provided that reduce or minimize the need for tubes, mass transfer packing, and/or heat transfer media, thereby reducing component parts that are known to foul and plug. Such an improved ethanol plant requires less regular maintenance and cleaning and thus, decreases the typical expense associated therewith. The provided improved ethanol plant designs, processes and methods may be retrofit into the existing plant or process (depending on the existing ethanol plant or process design) to reduce condensing load on existing or new evaporators, reduce the energy used to operate existing or new evaporators and/or reduce bottlenecks in the existing or new evaporators, are also provided. Accordingly, the provided improved ethanol plant designs, processes and methods cost relatively less to construct, install, operate and/or maintain relative to other known ethanol plants of similar capacity and/or process size.

The provided improved ethanol plant designs, processes and methods can improve water balance by utilizing what is typically considered excess or waste heat in a typical plant or process. Accordingly, the improved ethanol processes, plant designs and methods help improve water balance while also improving the typical production process (e.g., by cooling and/or concentrating thin stillage before the typical evaporation step or process is provided or applied, such as in a falling film evaporator).

The present disclosure relates to the application of an open column or other direct contact evaporator (DCE) at ethanol facilities to remove water from mash, whole stillage, thin stillage, syrup, and/or process condensate to improve fluid concentration and/or energy efficiency, while balancing water entering and leaving an ethanol plant.

In one aspect, the present disclosure provides for a method for ethanol production, the method comprising: providing thin stillage formed during ethanol production into an open column or other direct contact evaporator to help balance the water content of the thin stillage to form a concentrated thin stillage.

In another aspect, the present disclosure further provides for a method for ethanol production, the method comprising: providing process condensate formed during ethanol production into an open column or other direct contact evaporator to form a further condensed process condensate.

In another aspect, the present disclosure further provides for a method for balancing water content in a mixture, the method comprising: providing a mixture in an open column direct contact evaporator; and providing air in the open column or other direct contact evaporator to reduce the water content of the mixture through direct contact evaporation.

BRIEF DESCRIPTION OF THE DRAWINGS

Various examples of embodiments of the systems, devices, and methods according to this invention will be described in detail, with reference to the following figures.

It should be understood that the drawings are not necessarily to scale. In certain instances, details that are not necessary to the understanding of the invention or render other details difficult to perceive may have been omitted. It should be understood, of course, that the invention is not necessarily limited to the particular embodiments illustrated herein.

DETAILED DESCRIPTION

One or more specific illustrative embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

In a typical ethanol production process, whole stillage from a distillation process is centrifuged and/or decanted to form a liquid fraction called thin stillage and a solid fraction called wet distiller grains. The thin stillage is further condensed by removing water through a falling film evaporator to form syrup, which may or may not be applied to the wet distillers grains. However, water removal and syrup concentration are limited in the typical falling film evaporator due to fouling. While high efficiency forced circulation evaporation systems have been used to obtain a significantly greater syrup concentration, these approaches can be expensive to purchase, maintain and operate. Additionally, water balance is still impacted and must often be addressed in one way or another. The shortcomings of the typical and known evaporation process applications and associated water balance issues may be addressed by adding or introducing the example open column direct contact evaporator apparatus, step and/or process into the production process. Referring to the Figures, improved systems and methods for producing ethanol and more specifically, improving water balance and/or reducing energy use in ethanol production, are provided.

Figure 1:
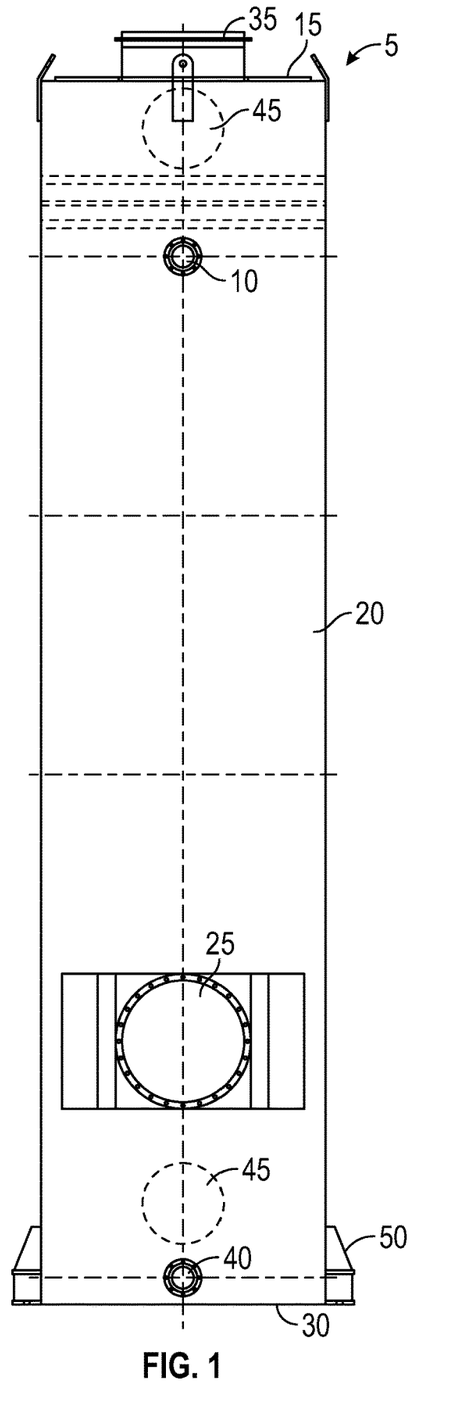
FIG. 1 depicts an example open column direct contact evaporator that may be used to remove water from liquids containing oils, solids or particulate.

FIG. 1 depicts an example open column direct contact evaporator 5 that balances water content of a fluid (e.g., a liquid, a mixture, a liquid including solids and particulate) using direct contact evaporation, whereby the entering liquid stream (e.g., process condensate, stillage or syrup) is cooled by evaporation of water into air entering the column at the bottom or some other location. The example open column direct contact evaporator 5 may be used with, for example, an ethanol production system as described further herein. The example open column direct contact evaporator 5 described herein may also be used with other applications to balance the water content of a liquid mixture or oil emulsion containing solids and/or particulate. The example open column direct contact evaporator 5 functions similarly to any direct contact evaporator, but has an open column, which open column does not require certain components of a direct contact evaporator that might otherwise be fouled, plugged or clogged by solids and/or particulate. Specifically, the open column direct contact evaporator 5 does not include any tubes, mass transfer packing, and/or heat transfer media, thereby eliminating the chance of fouling or plugging of these components. The example open column direct contact evaporator 5 requires less regular maintenance and cleaning than a direct contact evaporator. Thus, the open column direct contact evaporator 5 reduces the typical expense associated therewith. Furthermore, less downtime for cleaning may result in greater production yields.

In an example disclosed herein, the open column design allows for the open column direct contact evaporator 5 to be used with an ethanol production system to remove water from fluids that contain solids or oils. In particular, the open column direct contact evaporator 5 may be used to remove water from ethanol fluids such as mash, whole stillage, thin stillage, syrup, or process condensate using heat such as waste heat, steam, or any other energy source to provide heat, and make contact with such ethanol fluids to help evaporate or exhaust some of the water content while simultaneously increasing the fluid solids concentration. The open column direct contact evaporator 5 may be preferred over other types of direct contact evaporators for use with any liquids containing solids or particulate because the open column direct contact evaporator 5 tends to be relatively less expensive to install and maintain, while still providing the benefits of a direct contact evaporator.

The example open column direct contact evaporator 5 includes one or more spray nozzles (e.g., a fluid inlet) 10 located adjacent to a top 15 of the open column direct contact evaporator 5. The spray nozzle 10 sprays the liquid into the open column 20 of the open column direct contact evaporator 5. Meanwhile, air or similar media is being introduced into the open column 20 via an air inlet 25 adjacent to a bottom 30 of the open column direct contact evaporator 5. The air may be heated (or relatively warmer, or hot), dry air so that the air flowing through the open column direct contact evaporator 5 may better evaporate water from the liquid as the air flows through the open column 20, and to help control the exhaust temperature and humidity at an exhaust port 35 at the top 15 of the open column direct contact evaporator. The air exits the open column direct contact evaporator through an exhaust port (e.g., air outlet) 35 or vent at the top 15 of the open column direct contact evaporator 5. The air exiting the open column direct contact evaporator 5 is substantially saturated. Ideally, the air exiting the open direct column contact evaporator 5 is fully saturated to help maximize or optimize the amount of water removed from the liquid in the open column direct contact evaporator 5. A fluid outlet (e.g., a liquid outlet) 40 is adjacent to the bottom 30 of the open column direct contact evaporator 5. A concentrated version of the liquid may be expelled though the fluid outlet 40.

Additionally, the open column direct contact evaporator includes one or more access manways 45 to allow a user or operator to access an interior of the open column direct contact evaporator 5 for cleaning or maintenance. The example open column direct contact evaporator 5 is secured to the ground or a base using the correct number of anchor supports 50 as determined by design.

Figure 2:
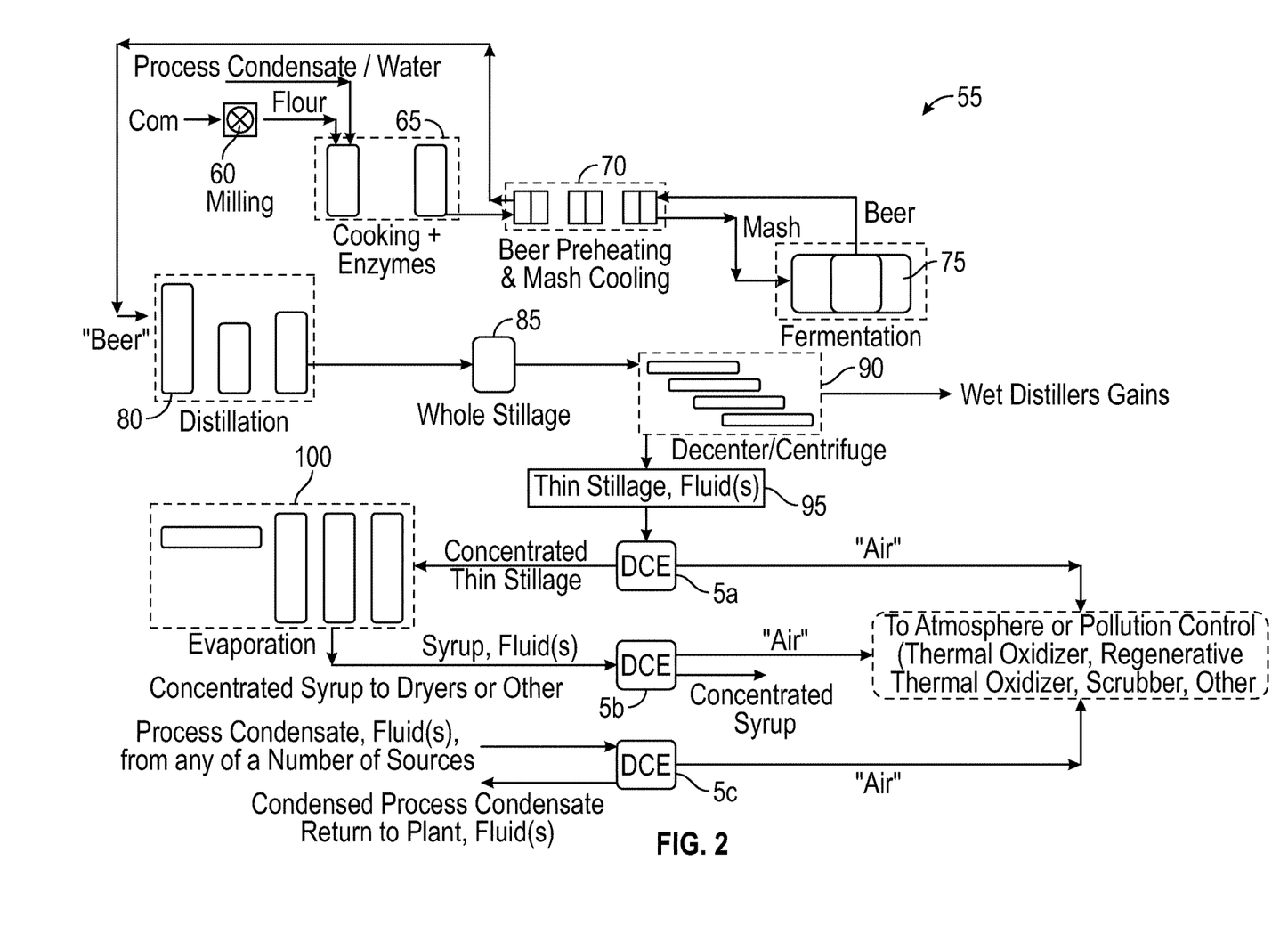
FIG. 2 depicts various areas in an ethanol production system whereby water is removed from process condensate, stillage or syrup using the example open column direct contact evaporator of FIG. 1.

FIG. 2 depicts an example ethanol production system and indicates the various places in which one or more example open column direct contact evaporators 5 of FIG. 1 may be provided and/or used. Specifically, FIG. 2 depicts an ethanol production system 55 in which the open column direct contact evaporator 5 is used to evaporate process condensate, mash, thin stillage or syrup. While an example open column direct contact evaporator is illustrated in FIG. 2, it will be appreciated that various types or embodiments of direct contact evaporators may be utilized.

A typical system 55 for producing ethanol may be provided or utilized up to the point of thin stillage processing. For example, the illustrated example depicts a system 55 which produces ethanol by milling a grain (e.g., corn) to form flour (e.g., via mill 60), cooking the flour with water to create a mash (e.g., in a cooking apparatus 65), cooling the mash (e.g., in a heat exchanger 70), fermenting the mash to create beer (e.g., in a fermentation tank 75), pre-heating the beer (e.g., in the heat exchanger 70), distilling the beer to form whole stillage (e.g., in a distillation apparatus 80), and decanting the whole stillage (which may be stored in a tank 85) into thin stillage (which may be stored in a tank 95) and wet distillers grains (e.g. in a decanter or centrifuge 90). The depicted typical system is not described in great detail herein, but any known system resulting in thin stillage may be provided or used. In an example ethanol production system 55, one or more open column direct contact evaporators 5a, 5b, 5c may be included to help balance the amount of water in the ethanol production.

The illustrated example in FIG. 2 depicts locations of multiple open column direct contact evaporators 5a, 5b, 5c that may be used alone or in combination in the ethanol production system 55. In the illustrated example, open column direct contact evaporators 5a, 5b may be positioned before and/or after the typical evaporation stage (e.g., a dryer or falling film evaporator 100). Additionally, in some examples, an open column direct contact evaporator 5c may be included to help or further condense process condensate, fluids, or any other fluids used in the ethanol production process.

In an example using an open column direct contact evaporator 5a before the typical evaporation stage (e.g., falling film evaporator 100), the open column direct contact evaporator 5a concentrates the thin stillage from the decanter or centrifuge 90 into a concentrated or more concentrated thin stillage. The thin stillage is provided into the open column direct contact evaporator via the fluid inlet (e.g., spray nozzle) 10 adjacent to the top 15 of the open column direct contact evaporator 5a, where heat (or hot air or other fluid) is utilized to effect evaporation of exhaust gases, vapor or air from the thin stillage to further concentrate the thin stillage. Dry air is streamed in from the air inlet 25 adjacent to the bottom 30 of the open column direct contact evaporator 5a to facilitate the evaporation of excess water from the thin stillage. In some embodiments, hot air is used to assist in the removal of excess water from the thin stillage and/or to control the humidity at the exhaust port 35. Additionally, the open column direct contact evaporator 5a helps cool the thin stillage, which exits the open column direct contact evaporator 5a through the fluid outlet 40 adjacent the bottom 30 of the open column direct contact evaporator 5a. The result is a concentrated or more concentrated thin stillage. The concentrated thin stillage is then provided to a typical evaporator 100, such as a known falling film evaporator.

The water is transferred from the thin stillage into exhaust gases, vapor or air (e.g., water laden air) due to a difference in water vapor pressures, thereby evaporating water from the thin stillage and/or cooling the thin stillage. The air exits the open column direct contact evaporator 5a substantially fully saturated. The gases, air or vapor may be directly discharged into the atmosphere (e.g., if permissible), treated by some pollution control device included with the open column direct contact evaporator 5a or directed to existing pollution control devices on site. In this way, in various embodiments, water is discharged or removed from the facility while benefit is gained from additional evaporation with a minimal energy input and operating cost.

While the open column direct contact evaporator 5a may not evaporate enough water from the thin stillage to produce a syrup, the concentrated thin stillage requires less additional processing to be transform into the desired syrup consistency. Because less additional processing is needed, less energy is required to condense the thin stillage to the syrup. The reduced energy use also reduces the cost to produce the ethanol and therefore can reduce the Carbon Intensity for ethanol production.

In examples using an open column direct contact evaporator 5b after the typical evaporation stage (e.g., a dryer, a falling film evaporation apparatus 100) of ethanol production, the syrup (i.e., corn syrup) is sprayed into the open column direct contact evaporator 5b. As the syrup is provided to the open column direct contact evaporator 5b, heat (or hot air or other fluid) is utilized to effect evaporation of exhaust gases, vapor or air from the syrup to further concentrate the syrup. Because of the denser consistency of the syrup, the spray nozzle utilized in connection with open column direct contact evaporator 5b may be of a different type and/or size than the spray nozzle utilized in connection with open column direct contact evaporator 5b. Additionally, the consistency of the syrup may require additional heat addition and/or additional attention from an operator to ensure that the open column direct contact evaporator is working efficiently.

As the syrup is sprayed into the open column direct contact evaporator 5b, relatively dry air (e.g., heated or relatively warmer or hot air) is streamed in from the bottom 30 of the open column direct contact evaporator 5b. As described above, the air helps evaporate excess water from the syrup, which results in a concentrated or more concentrated syrup exiting the open column direct contact evaporator 5b. Specifically, the water is transferred from the syrup into exhaust gases, vapor or air (e.g., water laden air) due to a difference in water vapor pressures, thereby evaporating water from the syrup and/or cooling the syrup. The gases, air or vapor may then be directly discharged into the atmosphere (e.g., if permissible), treated by some pollution control device included with the open column direct contact evaporator 5b or directed to existing pollution control devices on site. In this way, in various embodiments, water is discharged or removed from the facility while benefit is gained from additional evaporation with a minimal energy input and operating cost.

For some uses, the concentrated syrup may be desired over typical corn syrup. For example, if corn syrup is being shipped to a different facility for further processing, the concentrated syrup may be preferred because the shipping cost per weight of syrup is reduced due to the reduction of the water concentration.

In some applications, an open column direct contact evaporator 5c may be used to process condensate fluids from various sources in a typical ethanol production facility, method or process in a plant using air (e.g., hot air). In various embodiments, the water is transferred from the process condensate into exhaust gases, vapor or air (e.g., water laden air) due to a difference in water vapor pressures, thereby evaporating water from the process condensate. The gases, air or vapor may then be directly discharged into the atmosphere (e.g., if permissible), treated by some pollution control device included with the open column direct contact evaporator 5c or directed to existing pollution control devices on site. After the process condensate fluids are condensed, the fluids may be returned to other areas of the facility or otherwise for use in further ethanol production. In this way, in various embodiments, water is discharged or removed from the facility, method and process while benefit is gained from additional evaporation with a minimal energy input and operating cost. Specifically, the open column direct contact evaporator 5c cools water that may otherwise be disposed as waste water. Using an open column direct contact evaporator 5c for this application may help reduce waste water released from the plant (e.g., into the environment).

Introducing open column direct contact evaporators 5a, 5b, 5c into various parts of the ethanol production system 55 not only helps evaporate some of the additional water, but also uses some of the waste heat in this process. Using some of the waste heat means reducing the amount of energy spent in the system 55, and can lead to a reduction of cost. Thus, using an open column direct contact evaporator 5 can improve the overall energy efficiency in plants, such as the example ethanol production plant, and reduce the energy costs for the plant.

In some examples, the air used in the open column direct contact evaporator 5 may be air (or recycled air) originating, sourced from or used in various areas in the plant (e.g., waste heat). For example, the air may be from a small dryer. However, the air used in the open column or other direct contact evaporator 5 must be sufficiently dry (e.g., not humid, not saturated) such that the air can facilitate the evaporation of excess water from the liquid flowing through the open column direct contact evaporator 5. In various embodiments, the heat or air utilized by the open column direct contact evaporator 5 or evaporation process is at least partially provided by or sourced from dryers or other energy sources typically used in an ethanol production facility or process. It should be appreciated, however, that any waste heat, steam, or any other energy source may provide heat, and make contact with such ethanol fluids to help evaporate or exhaust some of the water content.

Alternatively or additionally, in some embodiments, an open column direct contact evaporator 5 is provided and/or utilized before the typical centrifuge or decanter apparatus 90 or step.

Figure 3A:
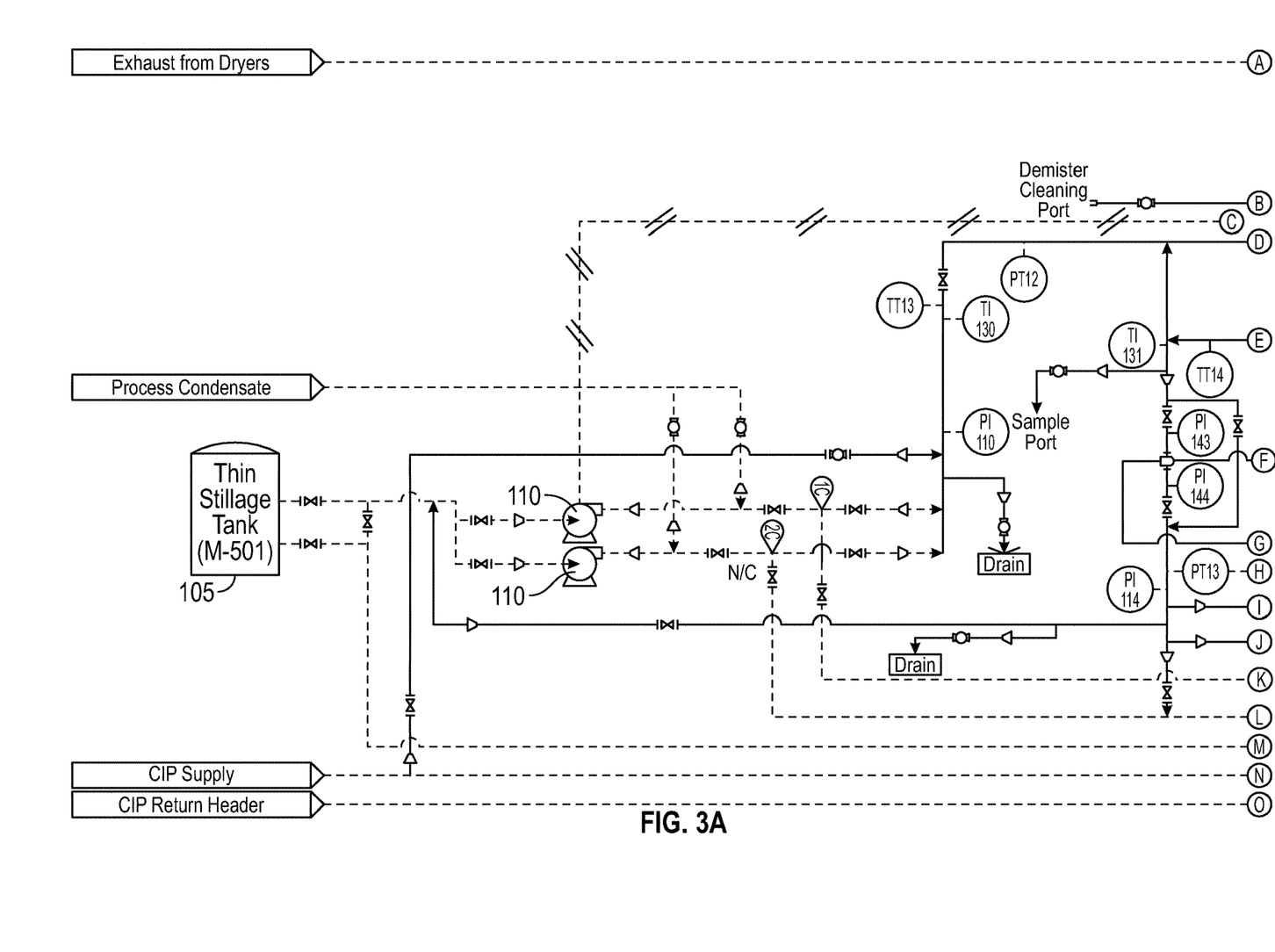
FIGS. 3A and 3B are a more detailed schematic of a portion of the example system to process stillage water of FIG. 2.
Figure 3B:
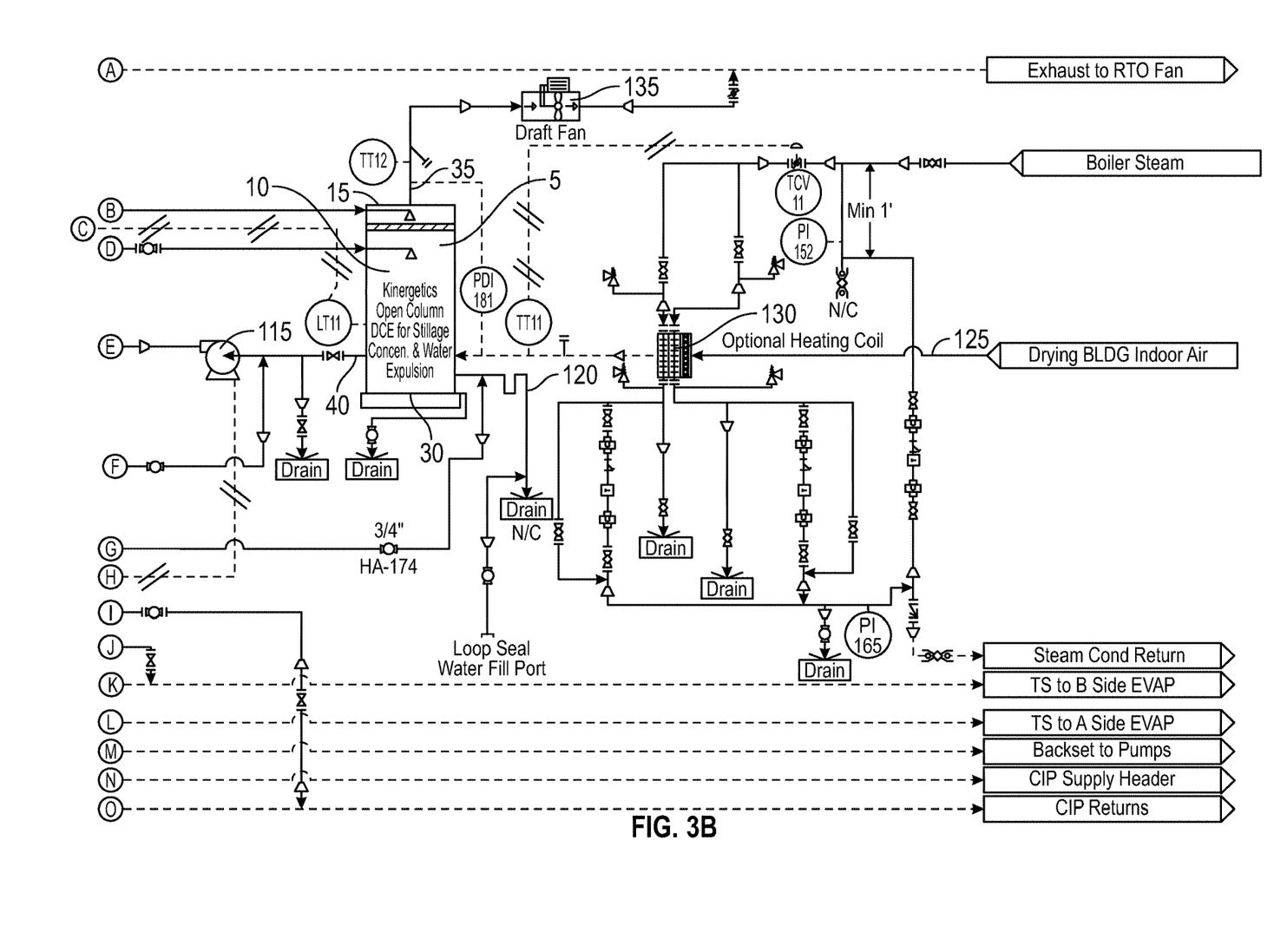

FIGS. 3A and 3B are a more detailed schematic of a portion of the example system 55 to process stillage water of FIG. 2. More specifically, FIGS. 3A and 3b are a portion of a P&ID used with one example ethanol production facility. The example schematic depicts only one example construction or implementation of an open column direct contact evaporator 5 used in a production facility and is only meant to be demonstrative and is not limiting the open column direct contact evaporator 5 to a single or specific use.

In the example depicted in FIGS. 3A and 3B, the open column direct contact evaporator 5 is being used to concentrate thin stillage. The thin stillage is stored in a thin stillage tank 105 until it is moved to the open column direct contact evaporator 5. From the thin stillage tank 105, the thin stillage is pumped to the spray nozzle 10 at the top 15 of the open column direct contact evaporator 5 using one or more pumps 110. The process of concentrating thin stillage in the open column direct contact evaporator 5 of this example schematic is substantially as described in conjunction with FIG. 2 above. The concentrated thin stillage exits the open column direct contact evaporator 5 adjacent the bottom 30 of the open column direct contact evaporator 5 and is pumped to one of a plurality of evaporators (e.g., dryers, falling film evaporators 100) via a pump 115. In some examples, the pump 115 may instead be operable to re-circulate the concentrated thin stillage through the open column direct contact evaporator 5. For example, the concentrated thin stillage may be recirculated if one pass through the open column direct contact evaporator 5 does not sufficiently reduce the water content to the desired concentration. Additionally, an overflow line 120 may be used to prevent flooding of the open column direct contact evaporator with concentrated thin stillage. The overflow line 120 may lead to a sump or drain.

Meanwhile, air (e.g., drying building indoor air 125) is being streamed through the open column direct contact evaporator 5. In some examples, the air first passes through a heating coil 130 or heater to heat the air to a desired temperature to better evaporate excess water from the thin stillage. A draft fan 135 positioned adjacent the air outlet 35 at the top 15 of the open column direct contact evaporator 5 helps keep the air moving through the open column direct contact evaporator 5 by pulling the air through the air outlet 35. That is, the draft fan 135 creates a back pressure on the system. In some examples, the draft fan 135 includes a heating coil 130 that uses steam to heat and expand the air to facilitate the back pressure on the system, though steam is not the only suitable heat source. The steam coil also prevents the moisture in the fully saturated air from the open column direct contact evaporator 5 from dropping out of the air as the saturated air mixes with drier air from dryers, which would negate the water balance control achieved by the open column direct contact evaporator 5. Additionally, the heating coil 130 may include a filter to prevent dust or particulate entering with the inlet air 125 from blocking the entrance to the heating coil 130.

Figure 4:
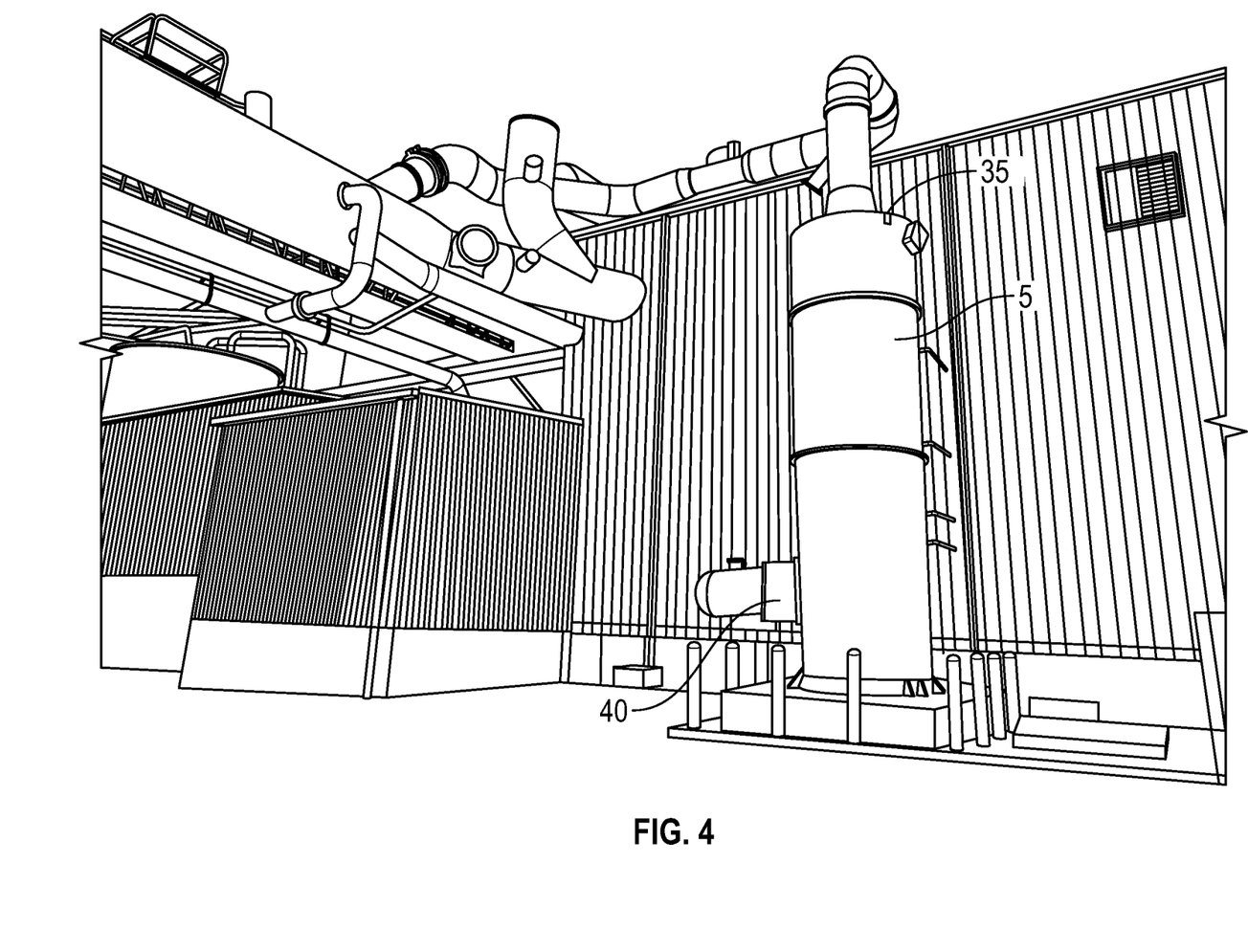
FIG. 4 is an example depiction of the open column direct contact evaporator integrated in an ethanol production system, such as the system illustrated in FIGS. 2 and 3.

FIG. 4 depicts the example open column direct contact evaporator 5 in use in the particular system to process stillage water as described in conjunction with FIGS. 3A and 3B. In this particular implementation, using the open column direct contact evaporator 5 reduced natural gas costs by nearly $600,000 per year compared to traditional evaporation methods. Additionally, in this particular construction, the exhaust air leaving the outlet of the open column direct contact evaporator 5 was fully saturated (i.e., 100% relative humidity), which indicates that the air was evaporating the maximum possible amount of excess water from the thin stillage.

As discussed above, use of a direct contact evaporator such as an open column direct contact evaporator is not limited to ethanol production, but can be used with any fluid containing solids or particulate. For example, an open column direct contact evaporator may be used in industrial wastewater evaporation and solvent/organic liquid recovery for use as an alternative fuel. Additionally, an open column direct contact evaporator may be used for water recovery and/or elimination from reverse osmosis (RO) concentrate. Another example used of an open column direct contact evaporator is with Black Liquor high concentration fluids in Kraft and similar pulp mill operations. With modifications, such as a filter to collect pollutants, an open column direct contact evaporator may be used in a chemical plant to evaporate excess water from the wastewater and concentrate the wastewater before shipping off for disposal, thus reducing shipping costs by reducing the amount of water being shipped.

One or more of the disclosed embodiments, alone or in combination, may provide one or more technical effects including a more efficient method of balancing the water content of a liquid containing solids or particulate. The disclosed designs enable the use of an open column direct contact evaporator to balance the water content of the liquid without fouling or plugging. The disclosed open column direct contact evaporator apparatus, systems, and methods for use may offer improved efficiency and reduced cost compared to other battery module designs. The technical effects and technical problems in the specification are exemplary and are not limiting. It should be noted that the embodiments described in the specification may have other technical effects and can solve other technical problems.

As utilized herein, the terms "approximately," "about," "substantially", and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed are considered to be within the scope of the invention as recited in the appended claims.

It should be noted that references to relative positions (e.g., "top" and "bottom") in this description are merely used to identify various elements as are oriented in the Figures. It should be recognized that the orientation of particular components may vary greatly depending on the application in which they are used.

For the purpose of this disclosure, the term "coupled" means the joining of two members directly or indirectly to one another. Such joining may be stationary in nature or moveable in nature. Such joining may be achieved with the two members or the two members and any additional intermediate members being integrally formed as a single unitary body with one another or with the two members or the two members and any additional intermediate members being attached to one another. Such joining may be permanent in nature or may be removable or releasable in nature.

It is also important to note that the construction and arrangement of the system, methods, and devices as shown in the various examples of embodiments is illustrative only, and not limiting. Although only a few embodiments have been described in detail in this disclosure, those skilled in the art who review this disclosure will readily appreciate that many various alternatives, modifications, variations, improvements and/or substantial equivalents, whether known or that are or may be presently foreseen, are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited. For example, elements shown as integrally formed may be constructed of multiple parts or elements show as multiple parts may be integrally formed, the operation of the interfaces may be reversed or otherwise varied, the length or width of the structures and/or members or connector or other elements of the system may be varied, the nature or number of adjustment positions provided between the elements may be varied (e.g. by variations in the number of engagement slots or size of the engagement slots or type of engagement). The order or sequence of any process or method steps may be varied or re-sequenced according to alternative embodiments. Other substitutions, modifications, changes, and omissions may be made in the design, operating conditions, and arrangement of the various examples of embodiments without departing from the spirit or scope of the present inventions. Therefore, the invention is intended to embrace all known or earlier developed alternatives, modifications, variations, improvements and/or substantial equivalents.

The technical effects and technical problems in the specification are exemplary and are not limiting. It should be noted that the embodiments described in the specification may have other technical effects and can solve other technical problems.

What is claimed is:

1. A method for processing stillage water formed in ethanol production, the method comprising:
   providing thin stillage formed during ethanol production into a direct contact evaporator to form a concentrated thin stillage.

2. The method for processing stillage water formed in ethanol production of claim 1, further comprising providing the concentrated thin stillage into a falling film evaporator.

3. The method for processing stillage water formed in ethanol production of claim 1, further comprising providing the concentrated thin stillage into a falling film evaporator to form a syrup from the concentrated thin stillage.

4. The method for processing stillage water formed in ethanol production of claim 3, wherein the syrup is concentrated using a second direct contact evaporator.

5. The method for processing stillage water formed in ethanol production of claim 1, wherein the direct contact evaporator is an open column direct contact evaporator.

6. The method for processing stillage water formed in ethanol production of claim 5, further comprising providing the concentrated thin stillage into a falling film evaporator.

7. The method for processing stillage water formed in ethanol production of claim 5, further comprising providing the concentrated thin stillage into a falling film evaporator to form a syrup from the concentrated thin stillage.

8. The method for processing stillage water formed in ethanol production of claim 7, wherein the syrup is concentrated using a second direct contact evaporator.

9. The method for processing stillage water formed in ethanol production of claim 1, whereby the direct contact evaporator forms the concentrated thin stillage using waste or excess heat formed in ethanol production.

10. The method for processing stillage water formed in ethanol production of claim 7, whereby the second direct contact evaporator forms the syrup using waste or excess heat formed in ethanol production.

\* \* \* \* \*